(12) United States Patent
Woo et al.

(10) Patent No.: US 7,985,848 B2
(45) Date of Patent: Jul. 26, 2011

(54) PHARMACEUTICAL COMPOSITION FOR PREVENTING AND TREATING DIABETES OR GLUCOSE CONTROL ABNORMALITY COMPRISING GINSENOSIDES

(75) Inventors: Sung-Sick Woo, Seoul (KR); Dong-Seon Kim, Daejeon (KR); Seon-Gil Do, Chungcheongbuk-do (KR); Young-Chul Lee, Daejeon (KR); Mi-Sun Oh, Chungcheongnam-do (KR); Ji-Min Cha, Seoul (KR); Jong-Han Kim, Gyeongsangnam-do (KR); Tae-Woo Kim, Ulsan (KR)

(73) Assignee: Unigen, Inc., Chungcheongnamdo (KR)

( * ) Notice: Subject to any disclaimer, the term of this patent is extended or adjusted under 35 U.S.C. 154(b) by 610 days.

(21) Appl. No.: 11/908,947

(22) PCT Filed: Mar. 17, 2006

(86) PCT No.: PCT/KR2006/000985
§ 371 (c)(1),
(2), (4) Date: Nov. 26, 2007

(87) PCT Pub. No.: WO2006/098604
PCT Pub. Date: Sep. 21, 2006

(65) Prior Publication Data
US 2008/0234207 A1     Sep. 25, 2008

(30) Foreign Application Priority Data

Mar. 18, 2005 (KR) .................. 10-2005-0022781

(51) Int. Cl.
*A61K 31/7032* (2006.01)
*A61K 31/7034* (2006.01)
*C07J 1/00* (2006.01)
*A01N 45/00* (2006.01)

(52) U.S. Cl. ............................................. 536/5; 514/26
(58) Field of Classification Search ........................ None
See application file for complete search history.

(56) References Cited

U.S. PATENT DOCUMENTS

| 5,776,460 | A * | 7/1998 | Kim et al. ...................... 424/728 |
| 6,083,932 | A | 7/2000 | Pang et al. |
| 2003/0190377 | A1 | 10/2003 | Kim et al. |
| 2003/0190378 | A1 | 10/2003 | Kim et al. |
| 2004/0202731 | A1 | 10/2004 | Gow et al. |
| 2008/0311169 | A1 | 12/2008 | Woo et al. |
| 2011/0052730 | A1 | 3/2011 | Woo et al. |

FOREIGN PATENT DOCUMENTS

| JP | 62-158490 A | 7/1987 |
| WO | WO-97/18824 A1 | 5/1997 |
| WO | WO 03/086438 | 10/2003 |
| WO | WO2005/120535 | * 12/2005 |
| WO | WO-2005/120535 A1 | 12/2005 |

OTHER PUBLICATIONS

Kang et al., "Increase in the Free Radical Scavenging Activity of Ginseng by Heat-Processing" Biological and Pharmaceutical Bulletin (2006) vol. 29 No. 4, pp. 750-754.*
The Merck Manual of Diagnosis and Therapy, published 1999 by Merck Research Laboratories, pp. 165-169 and 180-185.*
Merriam-Webster's Collegiate Dictionary, Tenth Edition, copyright 1998 by Merriam-Webster incorporated, p. 924.*
ISR issued issued Jun. 29, 2006 in PCT/KR2006/000985.
Written Opinion issued Jun. 29, 2006 in PCT/KR2006/000985.
Office Action (final) issued Mar. 24, 2010 in U.S. Appl. No. 11/629,086.
Office Action issued Sep. 2, 2009 in U.S. Appl. No. 11/629,086.
U.S. Appl. No. 12/866,859, filed Aug. 9, 2010, Wo et al.
Office Action issued Mar. 10, 2011 in U.S. Appl. No. 11/629,086.
Park et al. (2002) Arch. Pharm Res. 25(4):428-432, "Three New Dammarane Glycosides from Heat Processed Ginseng".
Office Action issued Sep. 10, 2010 in U.S. Appl. No. 11/629,086.

* cited by examiner

*Primary Examiner* — Eric S Olson
(74) *Attorney, Agent, or Firm* — Swanson & Bratschun, L.L.C.

(57) ABSTRACT

The present invention relates to a composition for preventing or treating diabetes or blood glucose control abnormality comprising gisenosides Rg3, Rg5, and Rk1 from natural substances; a use of a mixture comprising gisenosides Rg3, Rg5, and Rk1 for the manufacture of a medicament for preventing or treating diabetes or blood glucose control abnormality; or a method for preventing or treating diabetes or blood glucose control abnormality by administering a therapeutically effective amount of mixture comprising gisenosides Rg3, Rg5, and Rk1 to a subject. The present composition can effectively prevent or treat diabetes, blood glucose control abnormality, and complication thereof.

5 Claims, 1 Drawing Sheet

PHARMACEUTICAL COMPOSITION FOR PREVENTING AND TREATING DIABETES OR GLUCOSE CONTROL ABNORMALITY COMPRISING GINSENOSIDES

RELATED APPLICATIONS

This application is a 35 U.S.C. §371 national phase application of PCT/KR2006/000985 (WO 2006/098604), filed on Mar. 17, 2006, entitled "Pharmaceutical Composition for Preventing and Treating Diabetes or Glucose Control Abnormality Comprising Ginsenosides," which application claims the benefit of Korean Patent Application Serial No. 10-2005-0022781, filed on Mar. 18, 2005.

TECHNICAL FIELD

The present invention relates to a composition for preventing or treating diabetes or blood glucose control abnormality comprising gisenosides Rg3, Rg5, and Rk1 having the following structural formulae; a use of a mixture comprising gisenosides Rg3, Rg5, and Rk1 for the manufacture of a medicament for preventing or treating diabetes or blood glucose control abnormality; or a method for preventing or treating diabetes or blood glucose control abnormality by administering a therapeutically effective amount of mixture comprising gisenosides Rg3, Rg5, and Rk1 to a subject:

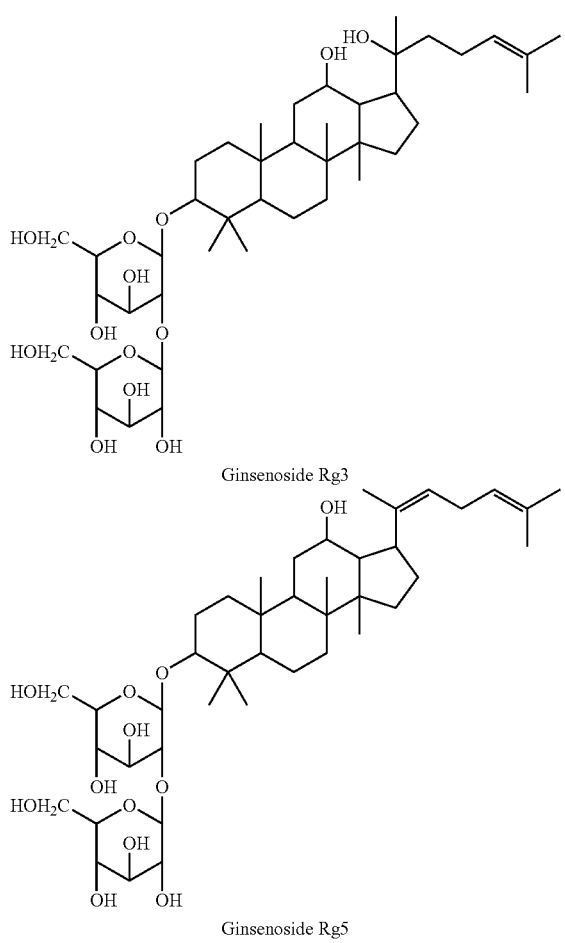

Ginsenoside Rg3

Ginsenoside Rg5

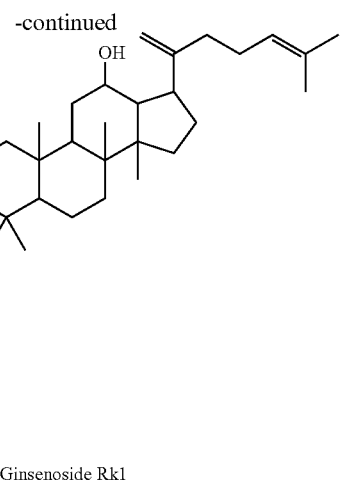

Ginsenoside Rk1

BACKGROUND ART

Many studies for treating and preventing diabetes have been conducted worldwide up to now, but the prevalence rate of diabetes has been steadily increased. Recently, the obesity population has been rapidly increased. The diabetes population is also expected to be rapidly increased due to inadequate life habits and aging.

The diabetes were roughly divided into insulin-dependent diabetes melitus and insulin-independent diabetes mellitus, but are now changed into Type 1 diabetes melitus and Type 2 diabetes melitus, respectively. It is known that Type 2 diabetes melitus occupying 90% or more diabetes patients is caused by dysfunction of insulin (resistance to insulin) or secreting defect of insulin. For its treatment, oral hypoglycemic agent or insulin formulation is used with diet and exercise.

Representative oral hypoglycemic agents are sulfonylurea promoting the secretion of insulin, metformin improving the resistance to insulin, glytazone, alpha glycosidase inhibitor inhibiting the absorption of glucose, etc.

Oral hypoglycemic agents having three kinds of pharmacological mechanisms are used in clinical trial, but their uses are restricted due to adverse effects such as hypoglycemia, toxicity of liver, weight increase, lacticacidemia, etc. Also, it is known that blood glucose can be controlled up to certain degree by actively using oral hypoglycemic agent or insulin formulation. However, two clinical test results recently completed on a large scale [The Diabetes Control and Complications Trial (DCCT) groups: *Eng J Med,* 2002, 342:381, The United Kingdom Prospective Diabets Study (UKPDS) groups: *JAMA,* 2002, 287:2542] are very negative thereto.

Despite active treatment of diabetes, a significant number of diabetes patients failed to attain the standard blood glucose level. Recently, medicines mixing and formulating medicines having different pharmacological mechanisms are in market from the conclusion that a medicine having one pharmacological mechanism has a limit to decrease the blood glucose to the normal level.

To successfully treat Type 2 diabetes mellitus having more complex pathogenesis than Type 1 diabetes mellitus, the development of a medicine having two or three pharmacological mechanisms, not one mechanism, has been required. In this point of view, it has been required to develop agents for preventing and treating diabetes from natural substances having various ingredients.

With rapidly increasing the obesity population, many people who do not show the characteristic symptoms of diabetes fail in the glucose tolerance test. These people are called as people showing impaired glucose tolerance (IGT), and it is known that a significant number of people among those showing IGT suffer from diabetes eventually. Therefore, the development of formulation which can block or delay the progress of diabetes in those people showing IGT is as important as early discovery of those showing IGT.

Blood glucose can be controlled by feedback of glucose, i.e., glucose absorbed to the human body is burnt at the peripheral tissue, or glucose stimulates beta cells to release insulin. In this regard, the ability capable of normally metabolizing glucose in the living body is called as glucose tolerance. Hyperglycemia may be caused by decrease of glucose tolerance.

In particular, ginseng among medicinal plants shows various physiological activities. Antidiabetic activity of ginseng was reported by many researchers, and Sotaniemi et al. and Vuksan, et al. (Sotaniemi et al., Diabetes Care, 1995, 18:1373, Vuksan et al., Arch Intern Med, 2000, 60:1009, Vuksan et al., Diabetes Care, 2000, 23:1221) reported the clinical test result about antidiabetic activity of *Panax quinquefolius*, and the animal test result about antidiabetic activity of *Panax ginseng* or *Panax quinquefolius*. However, as Vuksan et al. recently reported, even ginseng marketed by same company may show different antidiabetic activities experiment by experiment [Variable effects of American ginseng: a batch of American ginseng (*Panax quinquefolius L.*) with a depressed ginsenoside profile does not affect postprandial glycemia: *Eur J Clin Nutr*, 2003, 57(2):243-8].

These differences are because each ginseng has different amount or constitution of saponin, and it is not clearly known which ginsenoside of saponin has antidiabetic activity.

Thus, the present inventors have repeated antidiabetic tests in aged experiment animals, and conducted the glucose tolerance tests by using a composition consisting of a small amount of ginsenosides in red ginseng or ginseng, and then discovered that a mixture of ginsenosides Rg3, Rg5 and Rk1 shows superior blood glucose control effect to each ginsenoside, thereby completing the present invention.

DETAILED DESCRIPTION OF THE INVENTION

Technical Subject

The object of the present invention is to provide a new composition for preventing or treating diabetes or blood glucose control abnormality comprising gisenosides Rg3, Rg5, and Rk1 from natural substances; a use of a mixture comprising gisenosides Rg3, Rg5, and Rk1 for the manufacture of a medicament for preventing or treating diabetes or blood glucose control abnormality; or a method for preventing or treating diabetes or blood glucose control abnormality by administering a therapeutically effective amount of mixture comprising gisenosides Rg3, Rg5, and Rk1 to a subject.

MODE FOR CARRYING OUT THE INVENTION

Figure 1:
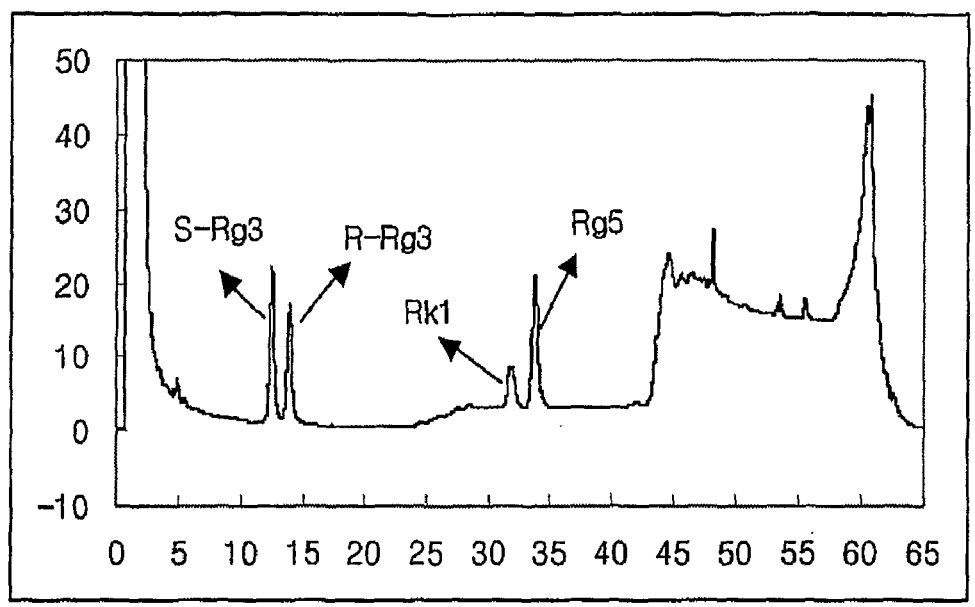
FIG. 1 is a chromatogram of ginsenoside Rg3, Rg5, and Rk1.

The present invention provides a composition for preventing or treating diabetes or blood glucose control abnormality comprising gisenosides Rg3, Rg5, and Rk1; or an extract of ginseng, red ginseng, or processed ginseng, having increased contents of gisenosides Rg3, Rg5, and Rk1 in water, $C_{1-4}$ alcohol, or mixing solvent thereof.

The present invention also provides a use of a mixture comprising gisenosides Rg3, Rg5, and Rk1; or an extract of ginseng, red ginseng, or processed ginseng, having increased contents of gisenosides Rg3, Rg5, and Rk1 in water, $C_{1-4}$ alcohol, or mixing solvent thereof, for the manufacture of a medicament for preventing or treating diabetes or blood glucose control abnormality.

The present invention also provides a method for preventing or treating diabetes or blood glucose control abnormality by administering a therapeutically effective amount of mixture comprising gisenosides Rg3, Rg5, and Rk1; or an extract of ginseng, red ginseng, or processed ginseng, having increased contents of gisenosides Rg3, Rg5, and Rk1 in water, $C_{1-4}$ alcohol, or mixing solvent thereof, to a subject.

In the present composition, the content ratio of gisenosides Rg3, Rg5, and Rk1 is not particularly limited, but preferably 1~10: 1~10: 1~10, respectively, and more preferably 1~7: 1~7: 1~5, respectively.

The above composition according to the present invention may use gisenosides Rg3, Rg5, and Rk1, or an extract of ginseng, red ginseng, or processed ginseng, having increased contents of gisenosides Rg3, Rg5, and Rk1.

The extract of ginseng or red ginseng is not particularly limited, but preferably an extract in water, $C_{1-4}$ alcohol such as methanol, ethanol, propanol, butanol, etc., or mixing solvent thereof, and may be prepared from undried ginseng according to conventional method.

In the present invention, ginseng may be selected from the group consisting of *Panax ginseng, P. japonicum, P. quinquefolium, P. notoginseng, P. trifolium* and *P. pseudoginseng*, and used without limit by root, stem, leaf, or herb.

The above extract of ginseng having increased contents of gisenosides Rg3, Rg5, and/or Rk1 may be prepared by treating root, leaf, rhizome, flower, tissue culture, or extract thereof in water or lower alcohol containing ginseng saponin with acid or enzyme, or at high temperature.

In one embodiment, the above processed ginseng may be prepared by, i) treating ginseng with acid at 50~80° C., and ii) steaming the treated ginseng at a temperature of 50~110° C. for 0.5~15 hr.

For example, the present composition is processed in two steps of: treating ginseng with acid at 50~80° C. ($1^{st}$ step) and steaming the treated ginseng of $1^{st}$ step at a temperature of 50~110° C. for 0.5~15 hr ($2^{nd}$ step). Such processed ginseng may contain an extract in water or common organic solvent, e.g., lower alcohol such as $C_{1-4}$ alcohol, or a lyophilized product thereof.

As shown above, the present composition may be prepared by additionally mixing powdered red ginseng or white ginseng with the processed ginseng extract or lyophilized product thereof, which is included in the scope of the present invention.

In the present invention, the acid that can be used in the $1^{st}$ step of the above processing method is not particularly limited so long as the acid can make substitution of the substituent located at $20^{th}$ carbon of the ginsenoside of ginseng, but preferably, acetic acid. In case of using acetic acid, the concentration of acetic acid is not particularly limited, but may be 20~100%. Particularly, it is preferable to use acetic acid because the boiling point of acetic acid is about 107° C., and so it can be removed in the steaming process without additional removal process.

In the acid treatment of the $1^{st}$ step, it is preferable for the steaming temperature to be about 50~80° C., more preferably 65~75° C., since the substitution by acid can be facilitated in the temperature range. Also, it is preferable to treat ginseng at 70° C. with acid for 0.1~10 hr, more preferable 1~5 hr, and particularly preferable 3 hr.

In the present invention, the processed ginseng is prepared by steaming the ginseng treated in the $1^{st}$ step at a temperature, particularly, under 110° C., for 0.5~15 hr. The processing method described in Korean Patent No. 96-17670 has a practical drawback that the range of temperature should be maintained at 120~180° C., which lowers economic efficiency. Thus, the present invention is much more convenient than the above patent method, and can increase the contents of ginsenosides Rg3, Rg5 and Rk1 with high yield because the ginseng in the present invention is steamed at a temperature of 50~100° C., preferably under 100° C., for 0.5~15 hr, preferably 0.5~8 hr, and more preferably 1~3 hr.

In the present invention, the extract or lyophilized product thereof used for the present composition may be prepared by conventional methods such as broth extraction or sonication with using solvents like water, $C_{1-4}$ alcohol such as methanol, ethanol, propanol, butanol, etc., or mixed solvents thereof, after the above $2^{nd}$ step.

The present composition improves diabetes or blood glucose control abnormality as shown in the following experimental example, and so can be used as an agent for preventing or treating diabetes, diseases relating blood glucose control abnormality, and complications thereof.

The composition of the present invention can be prepared according to conventional methods in the pharmaceutical field into conventional pharmaceutical preparations, for example, solution such as drinks, syrup and capsule, as an extract either in itself or by mixing it with a pharmaceutically acceptable carrier, excipient, etc.; and administered orally or parenterally. Preferably, the composition of the present invention may be orally administered in drink before and/or after a meal for quick effect.

Preferably, solution and capsule, et al. comprising the composition of the present invention may be used as medicine or health care products. Here, "health care products" mean food products prepared and processed in the form of tablet, capsule, powder, granule, solution, pill, jelly, etc., by using materials or ingredients having useful function to the human body.

The composition of the present invention is appropriately administered according to the extent of absorption of active ingredients into the body; excretion rate; age, weight, sex, and condition of patient; severity of treated disease; etc. However, generally, it is preferable to administer the present composition by 0.01~500 mg/kg, preferably, 0.1~200 mg/kg, 1~3 times a day.

Hereinafter, the present invention will be described in more detail with reference to the following examples, but the scope of the present invention should not be construed to be limited thereby in any manner.

EXAMPLES

A: Preparation of a Mixture of Ginsenosides Rg3, Rg5, and Rk1

1. Preparation of a Mixture of Ginsenosides Rg3 Rg5, and Rk1

100 g of powder of 70% ginseng ethanol extract was solved in 5 L of 50% acetic acid, hydrolysed at 65° C. for 2 hr, concentrated under decompression at 50° C., and dried under the vacuum to obtain 95 g of hydrolysis product. Chromatography was conducted to 50 g of the product on silica gel column by using methylene chloride/methanol/water (75:30:10, v/v, lower layer) as eluent, to obtain 8.7 g of fraction containing ginsenosides Rg3, Rg5, and Rk1. A mixture of ginsenosides Rg3, Rg5, and Rk1 was isolated from the above obtained fraction by conducting 15 times of Preparative HPLC, in 500 mg per time, under the following conditions, to obtain 2.7 g of the mixture.

TABLE 1

Isolation conditions of ginsenosides Rg3, Rg5, and Rk1

| Acetonitrile | Water | Flow rate (ml/min) |
|---|---|---|
| 0 | 48 | 52 | 5 |
| 40 | 48 | 52 | 5 |

Machine: HPLC
Column: Zorbax C18 19×250 mm
Temperature: 40° C.
UV: 203 mn

2. Contents Analysis of Ginsenosides Rg3, Rg5, and Rk1 in the Fraction containing the Ginsenosides The mixing fraction of gisenosides Rg3, Rg5, and Rk1 obtained above was analyzed under the following conditions by using Prep HPLC, thereby determining that the purity of the mixing fraction of gisenosides Rg3, Rg5, and Rk1 was 95% or more, and the content ratio of gisenosides Rg3, Rg5, and Rk1 was 1:1:0.3. This mixture was used for the following experimental examples.

TABLE 2

Quantitative analysis conditions of ginsenosides Rg3, Rg5, and Rk1

| | Acetonitrile | Water | Flow rate (ml/min) |
|---|---|---|---|
| 0 | 40 | 60 | 0.5 |
| 20 | 40 | 60 | 0.5 |
| 25 | 46 | 54 | 0.5 |
| 40 | 46 | 54 | 0.5 |

Machine: HPLC
Column: Capsell pak C18 MG 3×75 mm
Temperature: 40° C.
UV: 203 nm

B: Preparation of Processed Ginseng

1. Acetic Acid Treatment Process

The steaming instrument [Seogang ENG (Inc.), Korea], concentrator (EYELA, Japan), lyophilizer [Ilshinwrap (Inc.), Korea] used for preparing processed ginseng was owned by the Material Development Team of UNIGEN, Inc. Undried ginseng of 4-years-roots (Keumsan) was used as raw material for processing. Also, 95% or more anhydrous acetic acid [Samjeon Chemical (Inc.), Korea] was used as solvent for acetic acid reaction.

400 g of undried ginseng of 4-years-roots was quantified, and put into each of two plastic containers, and 1.5 L of 50% of acetic acid mixed with anhydrous acetic acid and water at the rate of 1:1, and 1.5 L of 100% of anhydrous acetic acid not mixed with water were put into each of the plastic container. One plastic container in the two plastic containers containing acetic acid was heated in water-bath at 70° C. for 3 hr, and the other plastic container was left at the room temperature for 24 hr without heating.

2. Steaming of Ginseng and Preparation of the Extract

The processed ginseng prepared in the above step B.1. was steamed and extracted for removal of acetic acid, addition of glucose, and hydrolysis, under the steaming temperature and time of 100° C. (3 hr). The processed ginseng was extracted with 70% of ethanol at 80° C. for 6 hr, and then extracted at 45° C. for about 5 hr.

To reduce the pumping effect due to the temperature increase and decompression during the lyophilization, the extracts, which are reactants with high viscosity (65-70 Brix), were diluted with warm water to lower the viscosity to about 24 Brix, and then the reactants were cooled at −70° C. for 2 days. When the cooling of the reactants was completed, the reactants were lyophilized at −70° C. and 10 mtorr for 2 days. The gisenosides content change according to the steaming process is shown in the following Table 3 [see FIG. 1].

TABLE 3

| Sample | Rb1 | Rb2 | Rc | Rd | Re | Rf | Rg1 | (R)-Rg3 | (S)-Rg3 | Rg5 | Rk1 |
|---|---|---|---|---|---|---|---|---|---|---|---|
| 10 | 0.43 | — | 0.53 | — | — | 0.04 | — | 17.35 | 15.37 | 31.33 | 11.89 |

Experimental Example

Antidiabetic Experiment to the Mixture of Ginsenosides R3, Rg5, and Rk1

1. Experimental Animal and Method

180~200 g of male Sprague-Dawley(SD) rats in the age of 6 weeks were purchased (Daehan biolink, Inc.) for confirming the effect of the composition for diabetes, in connection with aging, and bred at the Unigen's animal laboratory for 15 months or more. During the experiment, the breeding ground was kept at the temperature of 23±2° C. and relative humidity of 55±10%, and two animals were bred in a breeding box under the artificial lighting for 12 hr. Sterilized purified water was freely provided to the animals. Feed for experimental animals (Harlan, 2018S, Daehan biolink, Inc.) was used. Ten animals each were selected from the experimental animals in the age of over 15 months as control group and feeding group of the mixture of three ginsenosides, and adapted to the powder feed for 1 week, and then their daily consumptions of feed were measured. For two months the control group was fed only with powder feed which is powdered from solid feed, and the feeding group of the mixture of three ginsenosides was fed with powder feed in 20 mg/kg of the mixture of three ginsenosides, and both groups were allowed to freely drink sterilized purified water.

4 g/kg of glucose was solubilized in physiological saline solution to be 4 g/10 ml of concentration, and was orally administered to the animals with the sonde, for oral glucose tolerance test (OGTT). Before the administration of glucose, the animals were fasted for 16 hr, and then the blood glucose levels were measured. Then, glucose was administered, and the blood glucose levels in the blood taken from tail vein were measured at the time points of 15 min, 30 min, 60 min, and 120 min after the administration.

2. Statistic Analysis

All experimental results were shown by mean±SD, and Student's t-test was used to collect statistics, wherein statistical significance was determined on the basis of $p<0.05$.

3. Result and Interpretation

The control group was fed with powder feed only, and the feeding group of ginsenosides was fed with powder feed in 20 mg/kg of the mixture of three ginsenosides, for two months before the OGTT, and then the oral glucose tolerance test was conducted thereto.

Figure 2:
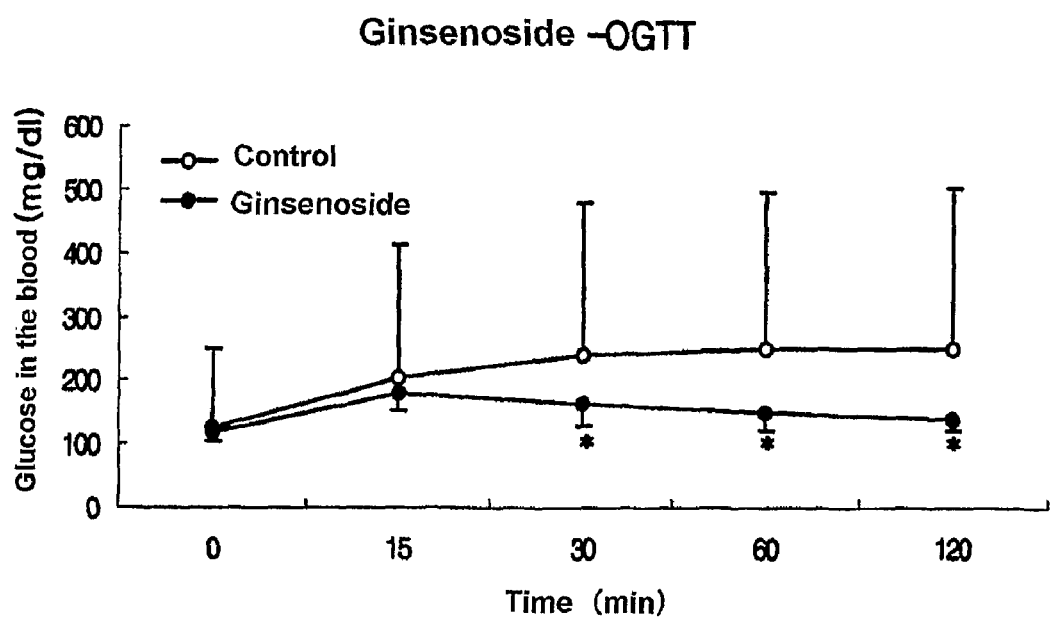
FIG. 2 is a graph showing the result of Oral Glucose Tolerance Test (OGTT) by administering the present composition for two months.

As shown in FIG. 2, the blood glucose levels of the two groups were about 110 before the oral administration of glucose, but were increased in time, i.e., over 200 in the control group, and about 160 in the feeding group of ginsenosides, at 15 min (*:$p<0.05$). The blood glucose level in the feeding group of ginsenosides was maximum, 160 at 15 min, and thereafter showed a decreasing tendency, but the blood glucose level in the control group showed a continuously increasing tendency in time. Particularly after 30 min, the blood glucose level in the feeding group of ginsenosides decreased, and showed statistic significance. The difference between blood glucose levels of the two groups became bigger in time after 30 min, which had statistic significance.

Blood glucose can be controlled by feedback of glucose, i.e., glucose absorbed to the human body is burnt at the peripheral tissue, or glucose stimulates beta cells to release insulin. In this regard, the ability capable of normally metabolizing glucose in a living body is called as glucose tolerance. Hyperglycemia may be caused by decrease of glucose tolerance. Therefore, the glucose tolerance test was conducted to the present subject for confirming the effect for blood glucose control of ginsenosides. As a result, the blood glucose levels in the control group after the administration of glucose increased twice as much as those before the administration of glucose, and the increased blood glucose level was maintained even after 2 hr from the administration. However, the blood glucose levels in the feeding group of ginsenosides increased right after the administration of glucose, but thereafter decreased to approach a normal concentration after 2 hr from the administration. Also, the increasing rate of blood glucose in the feeding group of ginsenosides was lower than that in the control group. And, none in the feeding group of ginsenosides died while two in the control group died by the glucose tolerance test.

| | |
|---|---|
| Mixture of ginsenosides | 1 g |
| Sugar | 10 g |
| Isomerized sugar | 10 g |
| Smell of lemon | proper quantity |
| Total amount after adding purified water | 100 ml |

The above-mentioned ingredients were mixed according to conventional preparation method for solution, and sterilized to give a solution.

Formulation Example 2

Preparation of Solution

| | |
|---|---|
| Mixture of ginsenosides | 2 g |
| Sugar | 10 g |
| Isomerized sugar | 10 g |
| Smell of lemon | proper quantity |
| Total amount after adding purified water | 100 ml |

The above-mentioned ingredients were mixed according to conventional preparation method for solution, and sterilized to give a solution.

Formulation Example 3

Preparation of Capsule

| Mixture of ginsenosides | 2 g |
|---|---|
| Lactose | 50 mg |
| Starch | 50 mg |
| Talc | 2 mg |
| Magnesium Stearate | proper quantity |

The above-mentioned ingredients were mixed, and filled in a gelatin capsule according to conventional preparation method for capsule to give a capsule.

Formulation Example 4

Preparation of Capsule

| Mixture of ginsenosides | 500 mg |
|---|---|
| Lactose | 50 mg |
| Starch | 50 mg |
| Talc | 2 mg |
| Magnesium Stearate | proper quantity |

The above-mentioned ingredients were mixed, and filled in a gelatin capsule according to conventional preparation method for capsule to give a capsule.

INDUSTRIAL APPLICABILITY

As known from the above, the present composition shows remarkable effect for preventing or treating diabetes or blood glucose control abnormality, and so diabetes and complication thereof can be prevented or treated by administering the present composition.

What is claimed is:

1. A process for preparing a composition for treating diabetes or lowering blood glucose levels comprising gisenosides Rg3, Rg5, and Rk1 comprising the steps of:
   (i) treating ginseng with 50% to 100% concentrated acid at 50-80° C.;
   (ii) steaming the treated ginseng at a temperature of from 50° C. to 110° C. for 0.5 to 15 hours; and
   (iii) extracting the processed ginseng.

2. The process for preparing a composition for treating diabetes or lowering blood glucose levels according to claim 1 wherein the temperature of the steaming is from 50° C. to lower than 110° C.

3. The process for preparing a composition for treating diabetes or lowering blood glucose levels according to claim 1 wherein the processed ginseng is extracted with a solvent selected from the group consisting of water, a $C_{1-4}$ alcohol, mixing solvent or a mixture thereof.

4. A method for lowering blood glucose levels comprising administering a therapeutically effective amount of a composition prepared by the process of claim 1 to a subject.

5. A method for treating diabetes by administering a therapeutically effective amount of a composition prepared by the process of claim 1 to a subject.

* * * * *

UNITED STATES PATENT AND TRADEMARK OFFICE
CERTIFICATE OF CORRECTION

| | | |
|---|---|---|
| PATENT NO. | : 7,985,848 B2 | Page 1 of 1 |
| APPLICATION NO. | : 11/908947 | |
| DATED | : July 26, 2011 | |
| INVENTOR(S) | : Sung-Sick Woo et al. | |

It is certified that error appears in the above-identified patent and that said Letters Patent is hereby corrected as shown below:

Col. 10, claim 3 should read as follows:

3. The process for preparing a composition for treating diabetes or lowering blood glucose levels according to claim 1 wherein the processed ginseng is extracted with a solvent selected from the group consisting of water, a $C_{1-4}$ alcohol, or a mixture thereof.

Signed and Sealed this
Thirteenth Day of September, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,985,848 B2 | Page 1 of 1 |
| APPLICATION NO. | : 11/908947 | |
| DATED | : July 26, 2011 | |
| INVENTOR(S) | : Sung-Sick Woo et al. | |

It is certified that error appears in the above-identified patent and that said Letters Patent is hereby corrected as shown below:

Col. 10, lines 22-26, claim 3 should read as follows:

3. The process for preparing a composition for treating diabetes or lowering blood glucose levels according to claim 1 wherein the processed ginseng is extracted with a solvent selected from the group consisting of water, a $C_{1-4}$ alcohol, or a mixture thereof.

This certificate supersedes the Certificate of Correction issued September 13, 2011.

Signed and Sealed this
Eleventh Day of October, 2011

David J. Kappos
*Director of the United States Patent and Trademark Office*